United States Patent
Arie Schols et al.

(10) Patent No.: US 11,020,423 B2
(45) Date of Patent: Jun. 1, 2021

(54) FOOD AND/OR FEED COMPOSITIONS FOR PREVENTING AND TREATING INFLAMMATORY DISEASES

(71) Applicant: DSM IP ASSETS B.V., Heerlen (NL)

(72) Inventors: Hendrik Arie Schols, Wageningen (NL); Paulus De Vos, Groningen (NL); Marco Alexander Van Den Berg, Kaiseraugst (CH); Geert Bruggeman, Drongen (BE); Erik Martinus Andrianus Maria Bruininx, Apeldoorn (NL); Neha Mohan Sahasrabudhe, Groningen (NL); Jan Scholte, Groningen (NL); Lingmin Tian, Wageningen (NL); Anton Johannes Scheurink, Groningen (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/696,637

(22) Filed: Nov. 26, 2019

(65) Prior Publication Data
US 2020/0188425 A1    Jun. 18, 2020

Related U.S. Application Data

(62) Division of application No. 15/741,584, filed as application No. PCT/EP2016/066222 on Jul. 8, 2016, now abandoned.

(30) Foreign Application Priority Data

Jul. 10, 2015  (EP) .................... 15176190

(51) Int. Cl.
*A61K 31/732* (2006.01)
*A23K 20/163* (2016.01)
*A23L 29/231* (2016.01)
*A23L 33/21* (2016.01)
*A61P 29/00* (2006.01)

(52) U.S. Cl.
CPC .......... *A61K 31/732* (2013.01); *A23K 20/163* (2016.05); *A23L 29/231* (2016.08); *A23L 33/21* (2016.08); *A61P 29/00* (2018.01); *A23V 2002/00* (2013.01)

(58) Field of Classification Search
CPC ..... A61K 31/732; A61P 29/00; A23K 20/163; A23L 29/231; A23L 33/21; A23V 2002/00
USPC ........................................ 536/115
See application file for complete search history.

(56) References Cited

U.S. PATENT DOCUMENTS

| | | | |
|---|---|---|---|
| 6,686,341 B1 * | 2/2004 | Bijlsma | A61P 25/00 514/54 |
| 8,722,107 B2 | 5/2014 | Staples et al. | |
| 8,722,111 B2 | 5/2014 | Staples et al. | |
| 9,149,430 B2 | 10/2015 | Reinhold | |
| 10,639,323 B2 * | 5/2020 | Bruggeman | A23K 20/163 |
| 2004/0223971 A1 | 11/2004 | Chang et al. | |
| 2006/0014719 A1 | 1/2006 | Chang | |
| 2009/0203799 A1 | 8/2009 | Reinhold | |
| 2011/0294755 A1 | 12/2011 | Eliaz | |

FOREIGN PATENT DOCUMENTS

| | | |
|---|---|---|
| EP | 1 550 448 | 7/2005 |
| WO | WO 03/080022 | 10/2003 |
| WO | WO 2004/091634 | 10/2004 |

OTHER PUBLICATIONS

Silva et al. Polysaccharide isolated from Passiflora edulis: Characterization and antitumor properties. Carbohydrate Polymers 87 (2012) 139-145. (Year: 2012).*
International Search Report for PCT/EP2016/066222, dated Oct. 19, 2016, 6 pages.
Written Opinion of the ISA for PCT/EP2016/066222, dated Oct. 19, 2016, 7 pages.
Arad et al., "Galectin-3 is a sensor-regulator of toll-like receptor pathways in synovial fibroblasts", Cytokine, May 2015, vol. 73, No. 1, pp. 30-35.
Kaczmarek et al., "Severity of doxorubicin-induced small intestinal mucositis is regulated by the TLR-2 and TLR-9 pathways", Journal of Pathology, vol. 226, No. 4, Mar. 2012, pp. 598-608.
Anonymous, "Product Specification: P9135 Pectin from Citrus Peel", Sigma-Aldrich, Nov. 26, 2012, p. 1, XP002762227.
Glossary of medical education terms, Institute of International Medical Education. http://www.lime.org/glossary.htm, Accessed in Mar. 2013. (Year: 2013).
Popov et al, Polypotency of the Immunomodulatory Effect of Pectins. Biochemistry (Moscow), 2013, vol. 78, No. 7, pp. 823-835 (Year: 2013).
Singthong et al, Structural characterization, degree of esterification and some gelling properties of Krueo Ma Noy (Cissampelos pareira) pectin. Carbohydrate Polymers 58 (2004) 391-400. (Year: 2004).
Chen et al., "Suppression of endotoxin-induced proinflammatory responses by citrus pectin through blocking LPS signaling pathways" Biochemical Pharmacology vol. 72, No. 8, pp. 1001-1009 (2006).

\* cited by examiner

*Primary Examiner* — Yih-Horng Shiao
(74) *Attorney, Agent, or Firm* — Nixon & Vanderhye, PC

(57) ABSTRACT

This invention relates generally to compositions and methods for combating inflammatory disease and particularly to the use of food and/or feed compositions for preventing, reducing and/or treating inflammatory disorders, diseases, or discomforts, wherein the compositions comprising at least one specific pectin.

10 Claims, No Drawings

Specification includes a Sequence Listing.

FOOD AND/OR FEED COMPOSITIONS FOR PREVENTING AND TREATING INFLAMMATORY DISEASES

This application is a divisional of commonly owned U.S. application Ser. No. 15/741,584, filed Jan. 3, 2018 which is the U.S. national phase of International Application No. PCT/EP2016/066222 filed Jul. 8, 2016, which designated the U.S. and claims priority to EP Patent Application No. 15176190.5, filed Jul. 10, 2015, the entire contents of each of which are hereby incorporated by reference.

JOINT RESEARCH AGREEMENT

The claimed invention was made by, on behalf of, and/or in connection with one or more of the following parties to a joint university-corporation research agreement: Wageningen University Department Agrotechnology and Food Sciences, Universitair Medisch Centrum Groningen Department Pathology and Medical Biology, Rijksuniversiteit Groningen Department Neuroendorinology, DSM Food Specialties, Nutrition Sciences N.V., and Agrifirm Innovation Center, which is legally part of CCL B.V., a subsidiary of Agrifirm Group. The agreement was in effect on and before the date the claimed invention was made, and the claimed invention was made as a result of activities undertaken within the scope of the agreement.

REFERENCE TO SEQUENCE LISTING SUBMITTED ELECTRONICALLY

The content of the electronically submitted sequence listing (Name: 4662_3898_ST25.txt; Size: 789 bytes; and Date of Creation: Mar. 6, 2020) is incorporated herein by reference in its entirety.

This invention relates generally to compositions and methods for combating inflammatory diseases and particularly to the use of food and/or feed compositions for preventing, reducing and/or treating inflammatory disorders, diseases, or discomforts.

Inflammatory diseases (or also inflammation-related disorders) in human are for example diseases such as Alzheimer's, ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematous (SLE), nephritism, Parkinson's disease, ulcerative colitis, auto-immune disease, asthma, atopy, cardio-vascular disease, diabetes, immune senescence, ischemia/reperfusion injury of the heart or of kidneys, feline infectious peritonitis, mastitis, psoriasis, sepsis, systemic lupus erymathosis, tumour metastasis, and visceral or cutaneous Leishmaniasis. Also it can be used to prevent or cure pro-inflammatory events such as occur during the use of cytostatics for cancer treatment, or other discomfort during the use of drugs that causes visceral damage.

Most of these Diseases are Wide-Spread.

For example Arthritis is the most common cause of disability in the USA. More than 20 million individuals with arthritis have severe limitations in function on a daily basis. It can affect humans as well as animals. In the context of the present invention we use the term "patients" to describe the targeted individuals. These patients are susceptible to or suffering from inflammatory disease. Rheumatism or rheumatic disorder is a non-specific term for medical problems affecting the joints and/or connective tissue. The term "rheumatism" is still used in colloquial speech and historical contexts, but is no longer frequently used in medical or technical literature; there is no longer any recognized disorder simply called "rheumatism." The traditional term covers such a range of different problems that to ascribe symptoms to "rheumatism" is not to say very much. "Non-articular rheumatism," also known as "regional pain syndrome" or "soft tissue rheumatism," can cause significant discomfort and difficulty. Furthermore, arthritis and rheumatism between them cover at least 200 different conditions Rheumatism and arthritis are general terms for acute and chronic conditions characterized by inflammation and pain. Rheumatism is a general category of conditions characterized by inflammation and pain in muscles and joints, including arthritis. Arthritis is characterized by inflammation of joints that causes swelling and pain. Types of arthritis include osteoarthritis, rheumatoid arthritis, ankylosing spondylitis (AS), and systemic lupus erythematosus (SLE). Rheumatic conditions include infectious arthritis, rheumatoid arthritis, arthritis due to rheumatic fever, arthritis due to trauma or degenerative joint disease, myositis, neurogenic arthropathy, bursitis, fibromyositis and hydroarthrosis. The cause of such diseases in not always fully understood but may be the result of other degenerative diseases, trauma, or auto-immune diseases such as SLE. Inflammation also occurs as a defensive response to host invasion by foreign agents and mechanical trauma that results in an immune response, e.g., microbial agents such as bacterial and viruses, toxins, alarm molecules, and neoplasia.

What these diseases and conditions, examples of inflammatory diseases, share in common is inflammation and the resulting pain. Prior methods for preventing and treating inflammatory diseases have generally focused on pain-killing and anti-inflammatory drugs. Typical methods have focused on oral medications such as steroidal cortisone derivatives and numerous non-steroidal anti-inflammatory drugs (NSAIDs). Unfortunately, these drugs almost always exhibit undesirable side effects. Other efforts have focused on joint implants such as the knee or hip implants. These methods are lengthy and complicated surgical procedures that force the patient to undergo costly invasive surgery and a significant recovery period requiring a rigorous and costly regimen of physical therapy. There is, therefore, a need for new methods for preventing and treating inflammatory diseases that avoids the undesirable side effects and costly surgical procedures characteristic of previous methods for preventing and treating inflammatory diseases.

Another example in which the invention is applicable, is in managing or preventing disease and/or discomforts and/or unwanted side-effects caused by unhealthy diets or the use of drugs. For example mucositis is an inflammation in the small intestine caused by chemotherapy such as the commonly applied doxorubicin. This drugs is causing mucosal damage and release of intracellular molecules such as DNA, RNA and heat shock proteins (also called alarm molecules or danger associated molecular patterns) that cause a severe inflammatory response with mucositis as a consequence. This can be prevented or reduced by this invention. This is considered to be, but not limited to, an example of inflammatory responses as a consequence of unhealthy diets, use of pharmaceuticals or the use of drugs.

In animals gastrointestinal disturbances that involve inflammatory responses are widespread. In farm animals (pigs, poultry and ruminants) this phenomenon causes large economic losses. For example within the pig population total losses of all piglets born in the European Union amount to approximately 17% and a substantial proportion of these losses can be associated with infections via mucosal surfaces (Lallès et al., 2007, Proc Nutr Soc. 66(2):260-268). A transient anorexia in newly weaned pigs is considered a major cause of these problems that leads to gut dysfunction, increased sensitivity to enteric infections and diarrhea. Concomitant patho-physiological changes include 20-30% reduction in mucosal weight associated with villous atrophy (Lallès et al., 2004, Animal Research 53, 301-316), a compromised intestinal barrier function (Wijtten et al., 2011, Br J Nutr. 105(7):967-981), disturbances in the homeostasis of the gut microbiota (Bauer et al., 2006, Nutr Res Rev. 19(1):63-78) and in the anatomical and functional development of the immune system (Lallès et al., 2007, Proc Nutr Soc. 66(2):260-268). Also in poultry, enteric diseases significantly contribute to economic losses because of impaired animal performance, increased mortality, and reduced welfare of birds (Timbermont et al., 2011, Avian Pathol. 40(4): 341-347). Nonspecific enteritis, coccidiosis, viral infections, dysbacteriosis and bacterial infections have been identified as major intestinal diseases that cause wet litter in poultry (Hermans et al., 2006, Vet Rec. 158(18):615-622). Although there are some species related differences, the underlying patho-physiological changes are quite similar to those in pigs. For instance, small intestinal development in newly hatched broilers deteriorates at low feed intake levels (Wijtten et al., 2012, Acta Agriculturae Scandinavica Section A-Animal Science, 62(1), 1-12).

In the past, in-feed antibiotic growth-promoting agents were used prophylactically to prevent these kind of problems. Nowadays, the prophylactic use of several antibiotics in farm animals is banned in the European Union or under increased pressure by the public opinion in other countries such as the United States due to concerns about antibiotic residues in food and increased antibiotic resistance in pathogens. Hence, also for animals there is a need for new methods for preventing and treating gastrointestinal disturbances that involve inflammatory responses.

Surprisingly, it was found that a specific kind of pectin (in regard to its degree of esterification) is useful in preventing, reducing and/or treating inflammatory disorders, diseases, or discomforts.

By "preventing, reducing and/or treating inflammatory disorders, diseases, or discomfort" it is mainly meant:
minimizing the risk of contracting any of the above listed diseases, and/or
ameliorating the related symptoms, and/or
lessening pain or discomfort associated with any of the above listed diseases and/or
lengthen the time between episodes where any of the above listed diseases can occur and/or
improving human and animal overall health and welfare Pectin is a structural heteropolysaccharide contained in the primary cell walls of terrestrial plants. It is produced commercially as a white to light brown powder, mainly extracted from citrus fruits, and is used in food as a gelling agent, particularly in jams and jellies. It is also used in fillings, medicines, sweets, as a stabilizer in fruit juices and milk drinks, and as a source of dietary fiber. Pears, apples, guavas, quince, plums, gooseberries, oranges, and other citrus fruits contain large amounts of pectin, while soft fruits like cherries, grapes, and strawberries contain small amounts of pectin. But also other plant sources than fruits can comprise pectin. For example, pectin can be sourced from potato, soy, sugar beet, chicory, carrot, tomato, pea, parsnip, and (green) beans. All these lists are not exhaustive at all. Only the main sources are listed.

The following illustration shows parts of the structure of pectin as well as (partially) esterified pectin.

Structure of Pectin (Polygalacturonic Acid)

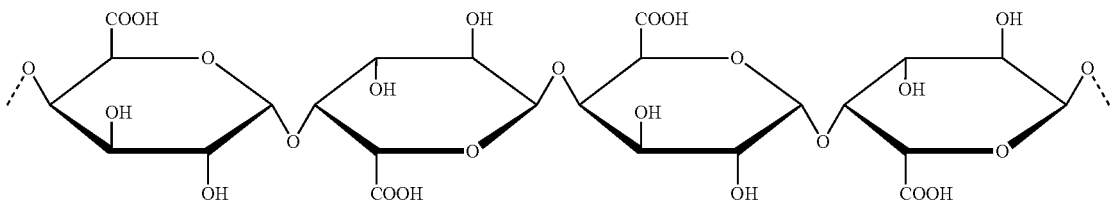

Structure of (Partially) Methylated Pectin

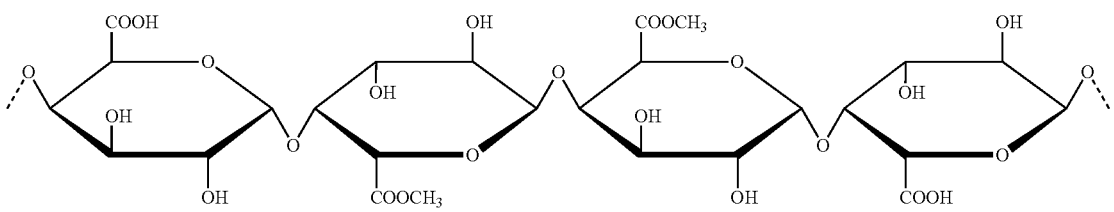

In the above shown formula the esterification is a methylation, but also other groups can be used (such as acetyl). Pectin can be esterified with one group (such as CH$_3$ or COCH$_3$) or with more than one group in the same oligomer structure. Acetylation usually occurs at the oxygen in the hydroxyl group on position 2 and/or 3, while methylation usually occurs at the carboxyl group on position 5.

In the scope of the present invention the degree of esterification is used to describe the percentage of esterified pectin monomer units in the backbone.

Pectin is a complex polysaccharide composed of a α-1, 4-linked D-galacturonic acid (GalA) backbone (the so-called homogalacturonan or smooth region) and segments consisting of alternating sequences of α-(1,2)-linked L-rhamnosyl and α-1,4-linked D-galacturonosyl residues ramified with side chains of arabinans, arabinogalactans and galactans (branched rhamnogalacturonans or hairy regions). Pectins are decorated with neutral sugars (NS), mainly being galactose and arabinose attached to the rhamnose moiety in the backbone.

Commercial pectins usually contain low amounts of neutral sugar as a result of the acid extraction (the neutral sugar content is around 5%). Other structural elements of pectins are xylogalacturonan and rhamnogalacturonan II. Rhamnogalacturonan II is carrying peculiar sugar residues such as Api (D-apiose), AceA (3-C-carboxy-5-deoxy-L-xylose), Dha (2-keto-3-deoxy-D-lyxo-heptulosaric acid) and Kdo (2-keto-3-deoxy-D-manno-octulosonic acid). The relative proportions of these different structural elements may vary significantly for different plant origins and the various derived commercial products.

The various structural elements of pectin can be esterified. The major types of esterification are: O-methyl, O-acetyl and O-feruloyl. Not excluding any other types of esterification. Most of the esterifications reside in the homogalacturonan region on the GalA residues. The GalA residues can be thus present with free carboxyl groups or esterified at one or more of the carboxyl groups. Esterification can occur as mono-esterification, but also as double esterification of single GalA residues. Not excluding any other numbers of esterification. The esterification on a single residue can be through a single type of alkyl group (i.e. methyl) or a single type of acyl group (i.e. acetyl). Not excluding any mixed type esterification. Thus, GalA can be methylated (leading to 0 or 1 methyl groups per GalA residue) or can be acetylated (leading to 0, 1 or 2 acetyl groups respectively on the oxygen of the hydroxyl group on the C-2 and/or C-3). The latter occurs as such in sugar beet and potato pectins.

The pectins of the current invention typically have a MW size distribution of 5 and 800 kDa. Preferably the MW size distribution is between 5 and 400 kDa. Preferably, the majority of the pectin molecules in a given pectin composition has a MW below 200 kDa. Preferably, the majority of the pectin molecules in a given pectin composition has a MW below 100 kDa.

The degree of esterification (DE) is by definition the amount of esters (in moles) present per 100 moles of total galacturonic acids (free GalA and substituted GalA summed together). As most commercial pectins are essentially having esterifications of the methyl-ester type, the DE is often expressed as the degree of methylation (i.e. DM). In that case, the degree of esterification is by definition the amount of methyl-esters (in moles) present per 100 moles of total galacturonic acids (free GalA and substituted GalA summed together). In the case that the esterification is of the acetyl type, the DE is often expressed as the degree of acetylation (i.e. DA). In that case, the degree of esterification is by definition the amount of acetyl-esters (in moles) present per 100 moles of total galacturonic acids (free GalA and substituted GalA summed together). In the case of multiple types of esterification in a single pectin sample, the DE is often expressed splitted in to a degree of methylation (i.e. DM) and a degree of acetylation (i.e. DA). These are calculated as described above. Alternatively, the DE can be expressed as the degree of esterification, defined the by amount of galacturonic acid residues modified with one or more esterifications—either being of the methyl or the acetyl type—(in moles) present per 100 moles of total galacturonic acids (free GalA and substituted GalA summed together).

In the context of this invention the term degree of esterification (DE) is used, and the percentages described are always based on the amount of GalA residues which are substituted through esterification (i.e. methylation). A DE of 50 means that 50% of all possible GalA residues are esterified (i.e. methylated).

The following patent application is related to the use of esterified pectins, more specifically it is related to the use of esterified pectins with a specific degree of esterification.

The following distinction is made among the esterified pectins:
(i) Low-esterified pectins
(ii) High-esterified pectins.

Low-esterified pectins have a degree of esterification (DE) of less than 50%. This means that less than 50% of the possible positions are esterified.

High-esterified pectins have a DE of more than 50%. This means that more than 50% of the possible positions are esterified.

DEs values for commercial HM-pectins typically range from 60 to 75% and those for LM-pectins range from 20 to 40% (Sriamornsak, 2003, Silpakorn University International Journal 3 (1-2), 206-228).

As mentioned above pectins are present in almost all higher plants. Several by-products of the food industries are used for their extraction, such as citrus peels (by-product of citrus juice production), apple pommace (by-product of apple juice manufacture), sugar beet (by-product of the beet-sugar industry) and in a minor extend potatoes fibres, sunflower heads (by-product of oil production) and onions (May, 1990, Carbohydr. Polymers, 12: 79-99). A typical process to extract HM pectins from the pomace or peels is in hot diluted mineral acid at pH1-3 at 50-90° C. during 3-12 hours (Rolin, 2002, In: Pectins and their Manipulation; Seymour G. B., Knox J. P., Blackwell Publishing Ltd, 222-239). Dry citrus peels contain 20 to 30% of pectin on a dry matter basis, lower amounts are present in dried apple pomace (10 to 15%) (Christensen, 1986, Pectins. Food Hydrocolloids, 3, 205-230). By adding alcohol (usually isopropanol but methanol or ethanol are also used) the pectins are precipitated. Finally, the gelatinous mass is pressed, washed, dried and ground (May, 1990, Carbohydr. Polymers, 12: 79-99). Depending on the process conditions, pectins with a DM from 55 to 80% are obtained (Rolin, 2002, In: Pectins and their Manipulation; Seymour G. B., Knox J. P., Blackwell Publishing Ltd, 222-239).

Low-methylated (LM) pectins can be obtained by de-esterification of high-methylated (HM) pectins mainly by controlling the acidity, the temperature and the time during extraction. To produce other types of pectins, esters can be hydrolysed by the action of acid or alkali either before or during an extraction, as concentrated liquid or in the alcoholic slurry before separation and drying. When alkali is used, the reaction has to be performed at a low temperature and in aqueous solutions to avoid β-eliminative degradation of the polymers (Kravtchenko et al, 1992, Carbohydrate Polymers, 19, 115-124). LM pectins can also be extracted with aqueous chelating agents such as hexametaphosphate (e.g. potato pectins) (Voragen et al., 1995, In: Food polysaccharides and their applications; Stephen A. M., New York: Marcel Dekker Inc, 287-339). The use of the enzyme pectin methyl-esterase (PME) for the production of LM pectins can be an alternative for the chemical extraction (Christensen, 1986, Pectins. Food Hydrocolloids, 3, 205-230). The conditions and time of the different reactions are varied leading to pectins with a different DE, even as low as a DE of zero.

Although, commercial LM pectins are almost exclusively derived from HM pectins, there are natural sources of LM pectin, such as mature sunflower heads (Thakur et al, 1997, Critical Reviews in Food Science and Nutrition, 37(1):47-73).

The DE Can be Determined by Commonly Known Methods.

For example, the degree of esterification can be determined using several methods such as titration (Food Chemical Codex, 1981), IR spectrometry (Gnanasambandam & Proctor, 2000, Food Chemistry, 68, 327-332; Haas & Jager, 1986, Journal of Food Science, 51(4), 1087-1088; Reintjes et al, 1962, Journal of food sciences, 27, 441-445) and NMR spectrometry (Grasdalen et al, 1988, Carbohydrate Research, 184, 183-191). Other methods using HPLC (Chatjigakis et al., 1998, Carbohydrate Polymers, 37, 395-408; Levigne et al., 2002, Food Hydrocolloids, 16(6), 547-550; Voragen et al, 1986, Food Hydrocolloids, 1(1), 65-70) and GC-headspace (Huisman et al, 2004, Food Hydrocolloids, 18(4), 665-668; Walter et al, 1983, Journal of Food Science, 48(3), 1006-1007) analysing the methanol content after saponification of the pectins have been developed. A capillary electrophoresis (CE) method has been developed to determine the DM of the polymers as such (Jiang et al, 2005, Food Chemistry, 91, 551-555; Jiang et al, 2001, of Agricultural and Food Chemistry, 49, 5584-5588; Zhong et al, 1998, Carbohydrate Research, 308, 1-8; Zhong et al, 1997, Carbohydrate Polymers, 32(1), 27-32). An advantage of the CE method is that the GalA content of the samples is not required to calculate the DM whereas the GalA values have to be known prior to the DM calculation following GC headspace and HPLC methods.

Surprisingly it was found that the use of at least one pectin with a DE of less than 65% was able to prevent, reduce and/or treat inflammatory disorders, diseases, or discomforts.

The pectins according to the present invention are preferably not amidated (no amide groups are in present in the pectin).

Furthermore it is surprising that this effect is achieved with a lower concentration of pectins when compared to the use of pectins known from the prior art. This leads to advantages in formulation, as lower concentrations of the current pectins are easier to formulate in to food and/or feed products.

Therefore the present invention relates to an esterified pectin or a mixture of esterified pectins for the use in the treatment of immune-mediated diseases and inflammatory diseases in patients, characterized in that the esterified pectin (or the mixture of esterified pectins) has a degree of esterification (DE) of less than 65%.

The degree of esterification in the context of the present invention is preferably determined by the HPLC method as described by A. G. J. Voragen, H. A. Schols and W. Pilnik, in the publication titled "Determination of the degree of methylation and acetylation of pectins by h.p.l.c,", published in Food Hydrocolloids, volume 1, issue 1, pages 65-70, 1986.

Furthermore the present invention relates to a method (M) of preventing, reducing and/or treating inflammatory disorders, diseases, or discomforts (lessening inflammatory diseases) by administering to patients esterified pectins (or a mixture of esterified pectins), wherein the pectins have a degree of esterification of less than 65%.

As illustrated by the examples pectins with a higher degree of esterification (more than the pectin of the present invention; i.e. a DE of 75) are far less effective, and only at higher pectin dosages.

In the context of the present the pectins can be obtained from any known sources. A list of suitable sources is given above. By using one of the processes as described above, the pectins with the correct DE are obtained.

Preferably the DE of the pectin (as a single compound or when used in a mixture) is less than 60%, more preferably less than 55%, especially preferred less than 50%.

Therefore the present invention also relates to an esterified pectin or a mixture of esterified pectins for the use in the treatment of immune-mediated diseases and inflammatory diseases, which is esterified pectin or a mixture of esterified pectins, wherein the pectin has a DE of less than 60%.

Therefore the present invention also relates to an esterified pectin or a mixture of esterified pectins for the use in the treatment of immune-mediated diseases and inflammatory diseases, which is esterified pectin or a mixture of esterified pectins, wherein the esterified pectin or a mixture of esterified pectins has a DE of less than 55%.

Therefore the present invention also relates to an esterified pectin or a mixture of esterified pectins for the use in the treatment of immune-mediated diseases and inflammatory diseases, which is esterified pectin or a mixture of esterified pectins, wherein the esterified pectin or a mixture of esterified pectins has a DE of less than 50%.

Therefore the present invention also relates to a method ($M_1$), which is method (M), wherein the pectin has a DE of less than 60%.

Therefore the present invention also relates to a method ($M_1'$), which is method (M), wherein the pectin has a DE of less than 55%.

Therefore the present invention also relates to a method ($M_1''$), which is method (M), wherein the pectin has a DE of less than 50%.

Usually the pectin has a DE of at least 1%, preferably of at least 2, more preferably of at least 3%. Therefore there is a range of 1-65%, 2-65%, 3-65%, 1-60%, 2-60%, 3-60%, 1-55%, 2-55% and 3-55%.

Commercial pectins can be a mixture of several populations: the distribution of the substituents can differ in an intramolecular level (within one single pectin polymeric chain) or in an intermolecular level (within one single pectin sample). This holds for all substituents, thus the sugars as well as the esterifications, and therefore both categories are meant with the word substituents' in the following. The substituents can be distributed completely at random. This random distribution can follow an even distribution pattern, when the substituents are regularly distributed over a single pectin polymeric chain, leading to a more homogenous pectin polymeric chain. If all pectin polymeric chains in a single pectin sample are of the same homogenous type, also the sample can be called homogeneous.

However, a single homogenous pectin polymeric chain can be present in a composition with other homogenous pectin polymeric chains but having a different intramolecular (but still homogeneous) distribution of the substituents. In this case, the pectin sample should be considered heterogeneous.

Furthermore it is also possible to modify the esterified pectin according to the present invention. One of the possible modifications is amidation. Amidated pectin is a modified form of pectin. In that case some of the galacturonic acid is converted with ammonia to carboxylic acid amide. This is done according to well-known processes. The presence of an amide group is typically at the C-6 position of the amidated GalA residues. If pectin is amidated, the DE is often expressed as the degree of amidation (i.e. DAM). In that case, the degree of esterification is by definition the amount of amides (in moles) present per 100 moles of total galacturonic acids (free GalA and substituted GalA summed together).

Other possible modifications of pectins are ethyl or propyl.

Preferably the esterification type of the pectin is either methylation and/or acetylation, more preferably methylation.

Therefore the present invention also relates to an esterified pectin or a mixture of esterified pectins as described above for the use in the treatment of immune-mediated diseases and inflammatory diseases, wherein the esterification type of the pectin is either methylation and/or acetylation Therefore the present invention also relates to an esterified pectin or a mixture of esterified pectins as described above for the use in the treatment of immune-mediated diseases and inflammatory diseases, wherein the esterification type of the pectin is methylation.

Therefore the present invention also relates to a method ($M_1$), which is method (M), wherein the esterification type of the pectin is either methylation and/or acetylation.

Therefore the present invention also relates to a method ($M_1'$), which is method (M), wherein the esterification type of the pectin is methylation.

Methods to characterize the different components (i.e. GalA content, neutral sugar content, degree of methyl-esterification, degree of actetylation, degree of amidation, distribution of the non-methyl-esterified GalA, molecular weight) of natural, modified as well as commercial pectins are well described in the PhD thesis of Stéphanie Guillotin (Studies on the intra- and intermolecular distributions of substituents in commercial pectins. Wageningen University, The Netherlands, 2005. ISBN 90-8504-265-8).

As described above the specific pectins are used to combating inflammatory disease of humans or animals.

The term "patient" means a human or other animal likely to develop or suffering from inflammatory disease, including avian, bovine, canine, equine, galline, feline, hircine, lapine, murine, musteline, ovine, piscine, porcine and vulpine animals. Preferably, the patient is a human, bovine, canine, feline, galline, ovine, porcine or avian.

The specific pectins according to the present invention are used—as disclosed above—to prevent, reduce and/or treat inflammatory disorders, diseases, or discomforts. This result is obtained by the fact that the specific pectins according to our invention are surprisingly able to bind TLR2, which is involved in many diseases, in regulation of the intestinal barrier function and in regulation of immune responses.

Toll-like receptors (TLRs) are a class of proteins that play a key role in the innate immune system. They are single, membrane-spanning, non-catalytic receptors usually expressed in sentinel cells such as macrophages and dendritic cells, that recognize structurally conserved molecules derived from microbes. Once these microbes have breached physical barriers such as the skin or intestinal tract mucosa, they are recognized by TLRs, which activate immune cell responses. The TLRs include TLR1, TLR2, TLR3, TLR4, TLR5, TLR6, TLR7, TLR8, TLR9, TLR10, TLR11, TLR12, and TLR13.

Surprisingly, it was found that only pectins with a low degree of esterification (i.e. low DE) are able to bind TLR2 in sufficient manner. Specifically, pectins with a low degree of methylation (i.e. low DM) are able to bind TLR2 in sufficient manner.

The interaction of the specific pectins according to our invention with TLRs was tested with cell based assays. In the context of the present invention HEK-Blue™ Detection (from InvivoGen) was used. The HEK-Blue™ system consists of various specific cell lines and cell culture medium developed to provide a fast and convenient method to monitor molecular interactions through so-called SEAP expression (see example 1 for details). This cell assay is commercially available. The results of these tests are disclosed in all details in the following examples. It was shown that low esterified (especially methylated) pectins show a surprising positive effect!

The amount of pectin, which is used can vary, depending on the patient. It must be an amount which shows a sufficient effect.

The pectin, which is ingested by the patient can be in any form. It is possible to use the pectin as such or in a mixture with other ingredients. When used in a mixture, the amount in this mixture is then depending on the other ingredients as well as the form of the mixture.

The ingredients which are used are usually chosen with regard to the use of the mixture. The ingredient can serve to improve the properties of the mixture or when the mixture is used to be formulated into a final composition to improve the final composition.

The ingredients can serve one or more purposes. It is clear that such ingredients must be food or feed grade (depending on its use).

The pectin can also be part of a food or feed product, whereas the food or feed product can be in any commonly known and used form.

The amount of pectin, which is used can vary (depending on the patient and/or inflammatory disease targeted). It depends on the body weight. Usually an amount between 0.01 and 5 g pectin with a DE of less than 65% per Kg body weight and per day is desired.

The amount pectin in a specific food or feed product usually varies dependent on the food or feed product. It is also dependent on how much a consumer/animals eat of this food or feed product. The amount in a food or feed product should be in such an amount that by a usual consumption of that food or feed product the necessary dosage of pectin is consumed.

The following examples serve to illustrate the invention.

EXAMPLES

Example 1

Pectin Inhibition of TLR2-Mediated NFkB Activation

Cell Lines and Cultivation

Cell lines were cultured in DMEM culture media (Lonza, Basel, Switzerland) with 10% decomplemented Fetal Calf serum, 50 U/ml Penicillin (Sigma, St. Louis, Mo., USA), 50

µg/ml Streptomycin (Sigma, St. Louis, Mo., USA) and 100 µg/ml Normocin (InvivoGen, Toulouse, France).

HEK-Blue™ TLR2-CD14 cells (InvivoGen, Toulouse, France) expressing human TLR2 and SEAP (Soluble Embryonic Alkaline Phosphatase) were used. NFκB and AP1 are stimulated to move to the nucleus in these cell lines when TLR2 is activated by an agonist. Here, the SEAP gene is under the control of a NFκB/AP-1 responsive promoter. Upon expression, the SEAP gene product is secreted in media and can be quantified using the Quantiblue (Invivo-Gen, Toulouse, France) solution. The enzyme converts the pink color into blue depending on the activity, and this can be measured with a spectrophotometer.

1× HEK-Blue™ Selection (InvivoGen, Toulouse, France) was added to the cultivation medium to control only the growth of the HEK-Blue™ TLR2-CD14 cells.

Pectin Sources

All pectins are isolated from citrus. Pectin with a DE of 0 was obtained from MP Biomedicals, LLC. The pectins with a DE of 7, 22, 45, 60 and 75 were obtained from CP Kelko.

Pectin Inhibition TLR2-1

HEK-Blue™ TLR2-CD14 cells were activated with the TLR2-1 specific agonist Pam3CSK4. Pectins of different DE values (0, 7, 22, 45, 60 and 75) were added at 0.5, 1 and 2 mg/ml. As a control HEK-Blue™ TLR2-CD14 cells were incubated with only pectin.

HEK-Blue™ TLR2-CD14 cells were seeded at 500,000 cell/ml in a 96 well plate with 100 µl volume per well. Cells were allowed to grow overnight. The following day, cells were treated with different pectins at different concentrations to study the effect on TLR2. After one hour of incubation with pectin, Pam3CSK4 was added at a concentration of 100 ng/ml. After 24 hrs of incubation at 37° C. with pectin and Pam3CSK4, the expression of the SEAP gene was determined. Supernatant of incubated cells was mixed with QUANTI-Blue solution in a ratio of 1:10. Presence of SEAP makes QUANTI-Blue turn blue. The NFκB activation was quantified by measuring the color intensity at 650 nm using an ELISA plate reader Versa Max (Molecular devices, Sunnyvale, Calif., USA). The assay was performed in 96 well plates with 8 technical repeats. Each experiment was repeated three times.

suggesting that at higher concentrations the absolute number of intra- or intermolecular regions with a local DE<65% (due to the possible irregular or heterogeneous distribution of esterified GalA residues throughout the pectin molecules and/or sample) becomes higher and therefore the inhibition of TLR2—through those regions with DE lower than 65—increases.

The viability of the HEK-Blue™ TLR2 CD14 was not affected by the additions of pectin (tested using WST-1 reagent).

Example 2

Pectin Binds to TLR2

Construction of the TLR2Ectodomain-HA Expression Plasmid

RNA was extracted from HEK-Blue™ hTLR2-CD14 cells using the RNeasy®Plus Mini kit (Qiagen, Venlo, Netherlands). cDNA was synthesized using OligodT primers (Life technologies, Carlsbad, Calif., USA), dNTP mix (Life technologies, Carlsbad, Calif., USA) and Superscript™III Reverse Transcriptase (Life technologies, Carlsbad, Calif., USA) according to the suppliers' manuals. TLR2 from codon1 to codon586 was synthesized using cDNA from HEK-Blue™ hTLR2-CD14 using the forward primer 5'-GCGCACCGGTATGCCACATACTTTGTGGATGG-3' (SEQ ID NO: 1), the reverse primer 5'-GCGCG-GATCCGTGACATTCCGACACCGAGAG-3' (SEQ ID NO: 2) and Pfu DNA polymerase (Thermo scientific, Waltham, Mass. USA). Primers were flanked by a GC doublet at the 5' end for restriction enzyme recognition. AgeI and BamHI restriction sites were included in the forward and reverse primer, respectively. The PCR product was digested with AgeI and BamHI restriction enzymes (Thermo scientific, Waltham, Mass. USA) and the plasmid pSELECT-CHA-blasti (InvivoGen, Toulouse, France) to create sticky ends. The PCR-amplified TLR2 ectodomain fragment and linear plasmid were ligated using T4 DNA Ligase (Thermo scientific, Waltham, Mass. USA). The ligated plasmid was used to transform One Shot TOP10 Chemically Competent E. coli (Life technologies, Carlsbad, Calif.,

| NFκB activation through TLR2-1 by Pam3CSK4 with and without pectin | | | | | | | |
|---|---|---|---|---|---|---|---|
| | 0.5 mg/ml | | 1 mg/ml | | 2 mg/ml | | Control (no Pam3CSK4) |
| Pectin type | NFκB activation | % inhibition | NFκB activation | % inhibition | NFκB activation | % inhibition | NFκB activation |
| — | 1.89 | 0 | 1.89 | 0 | 1.89 | 0 | n.a. |
| 0DE | 1.22 | 35.51 | 1.27 | 32.59 | 1.23 | 35.13 | 0.01 |
| 7DE | 0.99 | 47.64 | 0.77 | 59.15 | 0.81 | 57.05 | 0.15 |
| 22DE | 1.62 | 14.00 | 1.20 | 36.67 | 0.57 | 69.64 | 0.04 |
| 45DE | 1.75 | 7.33 | 1.32 | 30.12 | 0.64 | 66.22 | 0.03 |
| 60DE | 1.95 | 0 | 1.56 | 17.36 | 0.88 | 53.22 | 0.05 |
| 75DE | 1.96 | 0 | 1.88 | 0.52 | 0.85 | 54.93 | 0.13 |

Surprisingly, pectins are inhibiting TLR2, as determined by the color change of Quanti-blue at 650 nm through the level of SEAP activity after NFκB activation of the SEAP gene expression. The inhibition was highest with pectins with a low DE, but the inhibition was found with all DE values depending on the concentration of the respective pectin. The inhibiting effect of pectins with higher DE values (45, 60 and 75) was clearly concentration dependent, USA). Transformed E. coli cells were selected using Blasticidin agar media (InvivoGen, Toulouse, France). Obtained colonies were screened for correct orientation of the gene in the plasmid. Selected correct colonies were grown in blasticidin liquid media (InvivoGen, Toulouse, France) and the plasmid was isolated using the Qiagen Midi prep kit. Plasmid was then sequenced for selection of non-mutated clones (Baseclear, Leiden, Netherlands).

Transfection of HEK293T With the TLR2Ectodomain-HA Expression Fragment

HEK293T cells were seeded at 500,000 cells/ml in 12 well culture plates and incubated overnight. The following day, transfection was performed by using Lipofectamine LTX® (Life technologies, Carlsbad, Calif., USA). The sequence verified plasmid was linearized with the restriction enzyme NotI (Fast digest, Thermo Scientific, Waltham, Mass. USA). Purified, 1 μg linear plasmid was diluted in low serum media Opti-MEM® (Life technologies, Carlsbad, Calif., USA) and mixed with 3.5 μl of Lipofectamine LTX® (Life technologies, Carlsbad, Calif., USA). This transfection mix was incubated for 30 min at room temperature and then added to the previously seeded cells in the culture media. Cells were incubated with transfection medium mix for 24 hrs and transfected cells were selected using blasticidin in DMEM culture media (Lonza, Basel, Switzerland) with 10% decomplemented fetal calf serum, 50 U/ml Penicillin (Sigma, St. Louis, Mo., USA), 50 μg/ml Streptomycin (Sigma, St. Louis, Mo., USA) and 100 μg/ml Normocin (InvivoGen, Toulouse, France). Single cell clones were isolated to form the HEK293T TLR2ectodomain-HA cell line.

Cell Cultivation

Cell lines were cultured in DMEM culture media (Lonza, Basel, Switzerland) with 10% decomplemented Fetal Calf serum, 50 U/ml Penicillin (Sigma, St. Louis, Mo., USA), 50 μg/ml Streptomycin (Sigma, St. Louis, Mo., USA), 100 μg/ml Normocin (InvivoGen, Toulouse, France) and 50 μg/ml blasticidin (InvivoGen, Toulouse, France).

Protein Immunoprecipitation

Overnight grown HEK293T TLR2ectodomain-HA cells were lysed using 1× RIPA lysis buffer (Merck Millipore, Billerica, Mass., USA) in the presence of a protease inhibitor cocktail consisting of AEB SF (4-(2-Aminoethyl)benzenesulfonyl fluoride hydrochloride), Aprotinin, Bestatin, E-64, EDTA and Leupeptin (Sigma, St. Louis, Mo., USA) at 4° C. for 10 min followed by two times sonification for 5 seconds at 0% power. Supernatant was isolated after centrifugation at 14000 g for 10 min. TLR2ectodomain-HA tagged protein was immunoprecipitated using Pierce® Anti-HA Agarose (Thermo scientific, Waltham, Mass. USA) in a micro centrifuge tube. Protein was competitively eluted using HA synthetic peptide (Thermo scientific, Waltham, Mass. USA) by incubating two times for 15 min with a single bed volume of HA synthetic peptide at 30 C. Isolated protein was desalted and HA peptide was removed using Zeba Spin Desalting Columns and Devices, 40K MWCO (Thermo scientific, Waltham, Mass. USA). Isolated and desalted protein was quantified using Thermo scientific BCA protein assay kit.

ELISA for Binding of TLR2 and Pectin

The ELISA buffer was composed of 1 mM CaCl2 and 150 mM NaCl in 0.05M Tris buffer at pH 8.2. The buffer was used for washing as well as diluent for antibodies and pectin. The blocking buffer was made by dissolving 3% milk powder (FrieslandCampina, Amersfoort, The Netherlands) in ELISA buffer. For antibody solutions, a 1:2 dilution of blocking buffer with ELISA buffer was used for dissolving antibodies. ELISA plates (Corning, Tewksbury, Mass., USA) were treated with 50 μl of 50 μg/ml of Poly-L lysine for 1 hour at 37 C. Wells were washed once with 400 μl ELISA buffer. Pectins (0, 7, 22, 45 60 and 75DE) were dissolved in ELISA buffer at 1 mg/ml concentration and 50 μl was added to each well. The plates were incubated for 4 hours at 37 C to allow for binding of the pectin. Each well was then washed with 400 μl ELISA buffer and blocked overnight with 100 μl of blocking buffer at 4 C. After the blocking step, the ELISA plate was washed once with ELISA buffer. TLR2 ectodomain-HA fusion protein was applied to the pectin coated wells at 0.33 μg, 1 μg, 3 μg and 9 μg concentration per well. The ELISA plates were then incubated at 37 C for 3 hrs. The HA synthetic peptide was used as a negative control at 0.33 μg, 1 μg, 3 μg and 9 μg concentration per well, same as with the TLR2 ectodomaian-HA fusion protein. Pectin binding antibodies LM19 (specific for DE 0 and 7) and LM20 (specific for DE 22, 45, 60 and 75) from Plantprobes (Leeds, UK) were used as positive control for pectin binding at 1:100 dilutions. Afterwards, the wells were washed with 400 μl of ELISA buffer for 5 times and incubated with 50 μl primary detection antibody for the HA tag (Cell Signaling, Danvers, Mass., USA) in a 1:200 dilution. The primary antibody was incubated for 2 hours at 37 C. After primary antibody incubation, the plates were washed again 5 times with ELISA buffer. After washing, 50 μl of Biotin tagged secondary antibody (Southern Biotech, Birmingham, Ala., USA) was applied to each well at a 1:500 dilution. The Biotin tagged antibody was incubated for 1 hr at 37 C. This step was followed by 5 washings with 400 μl of ELISA buffer. Streptavidin-HRP (Dako, Heverlee, Belgium) (100 μl) was added to each well at a 1:1000 dilution. After incubation at 37 C for 1 hr, plates were washed 7 times with 400 μl of ELISA buffer. Finally, for detection, 100 μl of TMB substrate (Cell Signaling, Danvers, Mass., USA) was applied to each well and incubated at 37 C for 30 min. The reactions were stopped by adding 100 μl of stop solution (Cell Signaling, Danvers, Mass., USA). The ELISA plate was read at 420 nm in Plate reader Versa Max (Molecular devices, Sunnyvale, Calif., USA). For clarity sake the values of the negative control are subtracted from the values obtained with TLR2 ectodomain-HA.

| TLR2 ectodomain binding to pectin (a.u.) | | | | |
|---|---|---|---|---|
| Pectin type | 0.33 μg protein | 1 μg protein | 3 μg protein | 9 μg protein |
| 0DE | 0.03 | 0.15 | 0.45 | 1.43 |
| 7DE | 0.45 | 0.98 | 2.41 | 2.34 |
| 22DE | 0.03 | 0.16 | 0.49 | 0.81 |
| 45DE | 0.13 | 0.25 | 0.58 | 0.26 |
| 60DE | 0.07 | 0.09 | 0.16 | 0.07 |
| 75DE | 0.00 | 0.03 | 0.06 | 0.03 |

Surprisingly, pectins with low DE are directly binding to the TLR2 ectodomain, as indicated by the dose-dependent values obtained in the ELISA test.

Example 3

Pectin Inhibits Only the Pro-Inflammatory Pathway of TLR2 and Not Its Regulatory Pathway Cell Line HEK-Blue™ Null1 (InvivoGen, Toulouse, France) was seeded at 500,000 cells/ml in 12 well culture plates and incubated overnight. The following day, transfection was performed by using Lipofectamine LTX® (Life technologies, Carlsbad, Calif., USA). Plasmid pUNO3-hTLR2 (InvivoGen, Toulouse, France) was linearized with NotI (Thermo scientific, Waltham, Mass. USA). One μg of purified DNA was diluted in low serum media Opti-MEM® (Life technologies, Carlsbad, Calif., USA) and mixed with 3.5 μl of Lipofectamine LTX® (Life technologies, Carlsbad, Calif., USA). This transfection mix was incubated for 30 min at room temperature and then added to the previously seeded cells in the culture media. Cells were incubated with transfection medium mix for 24 hrs and transfected cells were selected using Zeocin (100 μg/ml) and Hygromycin B (150 μg/ml) in DMEM culture media (Lonza, Basel, Switzerland) with 10% decomplemented fetal calf serum, 50 U/ml Penicillin (Sigma, St. Louis, Mo., USA), 50 μg/ml Streptomycin (Sigma, St. Louis, Mo., USA) and 100 μg/ml Normocin (InvivoGen, Toulouse, France). Single cell clones were isolated. The thus obtained HEK-Blue™ Null1 TLR2 cell line expresses only TLR2 and not CD14.

TLR2 Activation and Inhibition Assay

HEK-Blue™ Null1 TLR2 cells were seeded at 500,000 cell/ml in a 96 well plate with 100 μl volume per well. Cells were allowed to grow overnight. The following day, cells were treated with different pectins to study the effect on TLR2. After one hour of incubation with pectin, the TLR2-6 specific agonist FSL-1 was added at a concentration of 100 ng/ml. After 24 hrs of incubation at 37 C with pectin and FSL-1, the expression of the SEAP gene was determined. Supernatant of incubated cells was mixed with QUANTI-Blue solution in a ratio of 1:10. Presence of SEAP makes QUANTI-Blue turn blue. The NFκB activation was quantified by measuring colorimetric readings at 650 nm using ELISA plate reader Versa Max (Molecular devices, Sunnyvale, Calif., USA). The assay was performed in 96 well plates with 10 technical repeats. Each experiment was repeated three times.

| | NFκB activation through TLR2-6 by FSL-1 with and without pectin | | | |
|---|---|---|---|---|
| Pectin type | 0.5 mg/ml NFκB activation | 1 mg/ml NFκB activation | 2 mg/ml NFκB activation | Control (no FSL-1) NFκB activation |
| — | 1.14 | 1.14 | 1.14 | n.a. |
| 0DE | 1.17 | 1.18 | 1.15 | 0 |
| 7DE | 1.05 | 1.05 | 1.08 | 0 |
| 22DE | 1.10 | 1.12 | 1.02 | 0 |
| 45DE | 1.13 | 1.11 | 1.03 | 0 |
| 60DE | 1.13 | 1.17 | 1.17 | 0 |
| 75DE | 1.13 | 1.13 | 1.20 | 0 |

The data shows that pectin does not inhibit the TLR2-6 signaling pathway as the stimulus in HEK-Blue™ Null1 TLR2 cells through FSL-1 is not changed by the presence of pectins, whereas the stimulation by Pam3CSK4 was clearly showing that pectin inhibits the TLR2-1 signaling response (example 1).

Example 4

Pectin in the Diet of Piglets Leads to a Reduced Intestinal Permeability of the Tight Junctions Piglet Feeding Trial Set-Up The experimental farm for young piglets is located in Flanders (Belgium) and consists of 8 batteries, each containing 4 pens. The piglets under study are hybrids of Topigs Piétrains and are weaned at 21 days. The piglets are weighed individually at weaning and 2 and 4 weeks after weaning. Feed intake is registered per pen of 4 piglets at the moments of weighing. At arrival the piglets are earmarked with a new Sanitel-number. During the trial, a veterinarian and a Felasa D certified person supervise the performed piglet experiment according to the international guidelines described in law EC/86/609.

Each pen (1.5 m×1.5 m) contains 4 piglets at the start of the trial. For each pen, one feeder (ad libitum) is installed for meal or pellets. One drinking nipple is installed per pen. The temperature at start is at 28±2° C. until 10 days after weaning. Afterwards, temperature is decreased to 25±2° C.

Commercial non-medicated diets are given. Non-medicated means that the piglet doesn't receive any therapeutic antibiotics before and during the trial. The diets are given in the form of meal. All feed were analysed for their nutritional content.

Four treatments were applied (diets A, B, C, D) on 7 replicates with 4 piglets per group. At the start of the trial, the piglets (around 7 kg body weight) are allocated to the different pens by weight. This allocation is made in order to have an equal average weight and an equal standard deviation around the average weight for each treatment and pen. For microbiological counting's and for taking biopsis, piglets receive an overdose of barbiturates (Nembutal) followed by sacrification. Afterwards, a section is performed on the piglets. Samples for microbial counts are immediately processed, while samples taken for histochemical experiments were fixed for later analysis. During the whole trial period the piglets are fed ad libitum, except for the period of microbiological countings. At that moment, three days before the microbiological countings are performed, the piglets are fed restricted. Piglets receive three times a day an amount of feed, which is carefully weighed and noted. The feed is given at 8.00, 13.00 and 18.00. When necessary, the sick piglets were treated individually (by injection). The following parameters were taken into account. (i) individual growth data, (ii) feed intake data per pen (corrected for eventual losses), (iii) feed conversion ratio during weaning, starter and whole trial period, (iv) fecal score and clinical score, (v) tight Junctions, (vi) microbial analysis, (vii) histochemical analysis.

Diets

Feed Compositions (in g/kg):

| Ingredient | Feed A | Feed B | Feed C | Feed D |
|---|---|---|---|---|
| Corn | 171.13 | 169.13 | 169.13 | 169.13 |
| Grains (wheat and barley) | 491.83 | 491.83 | 491.83 | 491.83 |
| Protein sources (soy, potato) | 227.72 | 227.72 | 227.72 | 227.72 |
| Milk derivatives (whey) | 52.65 | 52.65 | 52.65 | 52.65 |
| Soy bean oil | 14.19 | 14.19 | 14.19 | 14.19 |
| Amino acids | 10.80 | 10.80 | 10.80 | 10.80 |
| Minerals & trace minerals | 10.24 | 10.24 | 10.24 | 10.24 |
| Limestone | 10.63 | 10.63 | 10.63 | 10.63 |
| Enzyme* | 0.64 | 0.64 | 0.64 | 0.64 |
| Premix** | 10.17 | 10.17 | 10.17 | 10.17 |
| Pectin DE33 | — | 2.00 | — | — |
| Pectin DE55 | — | — | 2.00 | — |
| Pectin soybean meal | — | — | — | 2.00 |

*Xylanase/beta-glucanase and phytase cocktail (BASF)
**Premix includes aroma's, extra trace minerals, vitamins (Vitamex N.V.)

Pectin Sources

Pectins with a DE 33 and 55 were isolated from citrus and obtained from Herbstreith & Fox (Neuenbürg/Württingen, Germany). The Soy Bean Meal (SBM) was from South-American origin (mixture from Argentina, Brasil and/or Paraguay) and processed to extract the residing pectins by mixing the SBM at 33% dry matter with tapwater and autoclaving for 30 mins at 120 C. After cooling the obtained material was freeze dried and milled, and used as such in the diet.

Mannitol-Lactulose Test

The permeability of the ileum was quantified by performing a mannitol-lactulose test in the animals. Lactulose cannot pass an integer small bowel which is considered to be positive as there is a lower chance on systemic infections and immune issues.

Mannitol is a metabolically inert monosaccharide, which is passively absorbed through the intestinal mucosa. Any absorbed mannitol is fully excreted in the urine within a couple of hours. Mannitol was administered to the piglets through a stomach-pump at 0.3 g mannitol/kg body weight (4 hours before dissection). Lactulose is a metabolically inert disaccharide, which normally is not absorbed unless the mucosal barrier is compromised. Any absorbed lactulose is fully excreted in the urine within 6 hours. Lactulose was administered to the piglets through a stomach-pump at 0.75 g lactulose/kg body weight (4 hours before dissection)

During dissection piglet urine was then collected. In piglets with a healthy intestine, the mean absorption of lactulose is less than 1% of the administered dose. A recovery of >1% lactulose in the urine indicates a disaccharide hyperpermeability.

In piglets with a healthy intestine, the mean absorption of mannitol is >14% of the administered dose.

A recovery of <14% mannitol in the urine indicates a carbohydrate malabsorption.

A lower lactulose/mannitol ratio (L/M ratio) indicates a positive effect of a diet.

| Permeability test of the gastrointestinal tract (average of three individual pigs per diet) | | |
|---|---|---|
| Diet | L/M ratio | SD |
| A | 0.55 | 0.90 |
| B | 0.019 | 0.032 |
| C | 0.024 | 0.042 |
| D | 0.15 | 0.27 |

As shown all pectins, and especially the pectins with DE 33 and 55 pectin, lead to a reduced L/M ratio and thus have a positive effect in the small intestine of the young pigs Example 5

Pectin in Diets Lead to an Increase of the Villus to Crypt Ratio

The piglet feeding trial set-up was as described in example 4.

Sample Preparation for Histology

Sampling: Take a sample of the duodenum and/or ileum and rinse with physiological water (0.9% NaCl). Store in 20 ml formalin buffer (1 ml formaldehyde (37%)/liter). 4.5 g $NaH_2PO_4$+10.4 g $Na_2HPO_4$)

Bedding: Poor the paraffin solution in the recipient (not fully full) and place the intestinal sample vertical in the recipient. Let solidify at 4° C. and fill the recipient completely. Let solidify at −3° C.

Biopt: Clean scalpel with 10% xylene and let dry. Transfer coupe with brush and needle to 50% alcohol. Cut in pieces and transfer to distilled water (65° C.) with brush and microscope slide. Place sample on the microscope slide and incubate one night at 60° C.

Haematoxiline-eosine (H&E) staining steps at ambient temperature:
1). Deparaffinize
   Wash 3 times with 10% xylene (for 5 minutes)
   Wash 2 times with 100% ethanol (for 3 minutes)
   Wash once with ethanol 90% (for 3 minutes)
   Wash once with ethanol 70% (for 3 minutes)
   Wash once with water (for 3 minutes)
   Wash once with water (for 3 minutes)
2). staining
   Incubate in Mayers haematoxiline (for 6 minutes)
   Wash once with water (for 5 minutes)
3). counter-staining
   Incubate in 10% eosine (for 5 minutes)
   Wash 10 times with water (each for 30 seconds)
4). Dehydrate
   Wash 10 times with ethanol 90% (each for 30 seconds)
   Wash 10 times with ethanol 70% (each for 30 seconds)
   Wash 2 times with ethanol 100% (for 5 minutes)
   Wash 3 times with 10% xylene (for 5 minutes)

Quantification of the Villi Length and Crypt Depth

Above embedded histological samples are analysed by means of an Olympus microscope, and villi length (mm) and crypt (depth) are measured.

| Histological morphology of the gastrointestinal tract (average of 3 pigs per diet) | | | | |
|---|---|---|---|---|
| Diet | SI | Crypt (mm) | Villus (mm) | V/C ratio |
| A | Duodenum | 23.5 ± 3.3 | 36.6 ± 7.3 | 1.6 ± 0.3 |
|   | Ileum | 15.0 ± 0.8 | 22.0 ± 3.0 | 1.5 ± 0.2 |
| B | Duodenum | 23.7 ± 4.7 | 40.5 ± 3.5 | 1.8 ± 0.3 |
|   | Ileum | 15.2 ± 0.5 | 25.1 ± 0.7 | 1.7 ± 0.1 |
| C | Duodenum | 23.4 ± 1.9 | 42.5 ± 8.1 | 1.8 ± 0.4 |
|   | Ileum | 15.3 ± 1.2 | 26.7 ± 4.1 | 1.8 ± 0.1 |
| D | Duodenum | 23.8 ± 2.7 | 37.0 ± 3.9 | 1.6 ± 0.1 |
|   | Ileum | 15.2 ± 2.6 | 21.5 ± 1.7 | 1.5 ± 0.4 |

Longer villi imply a higher absorption capacity while longer crypts imply the opposite. Thus a higher villus to crypt ratio is considered to be a positive effect of a diet, while a lower villus to crypt ratio is considered to be a negative drawback for using the respective diet. As shown, especially the diets with pectin DE 33 and 55 have an enhanced villi-to-crypt ratio in both the duodenum and ileum, which demonstrate the potential of both pectins to improve gastrointestinal health.

Example 6

Pectin Acts as Anti-Inflammatory Agent in Doxorubicin Induced Mucositis

Mucositis, also referred to as mucosal barrier injury, is one of the most severe side effects of radiotherapy and chemotherapy treatment. Both inflammation and apoptosis of the mucosal barrier result in its discontinuity, thereby promoting bacterial translocation. Five phases are important in the pathophysiology of mucositis: (1) the formation of reactive oxygen species leading to the activation of nuclear factor kappa B (NFkB) during the initiation phase, (2) the induction of messenger molecules such as tumor necrosis factor alpha (TNFa), resulting in treatment-related tissue inflammation and apoptosis during the upregulation/message generation phase, (3) the amplification of messenger molecules in the amplification/signaling phase, leading to more inflammation and apoptosis, (4) discontinuity of the epithelial barrier resulting from apoptosis during the ulcerative phase, thereby promoting bacterial translocation, and (5) a spontaneous healing phase, characterized by cell proliferation (Sonis, 2004, Semin Oncol Nurs. 20(1):11-5); Van Vliet et al, 2010, PLoS Pathog. 6(5):e1000879).

Mice

C57B1L/6 female mice (7-10 weeks old) were purchased from Janvier laboratories, France. The experimental use of animals was approved by the Animal Ethical Committee of the University of Groningen. All the mice were acclimatized for 2.5 weeks prior to start of the experiment. Mucositis was induced by administration of doxorubicin (Sigma, St. Louis, Mo., USA).

DietsMice were supplied with ad-libitum RMH-B diet (AB diets, Woerden, The Netherlands). The ingredients of diet specified by supplier are wheat, meat meal (80% sterilized), yellow dent corn, whole oats, wheat middlings, alfalfa, soya oil, dried yeast, dicalcium phosphate, calcium carbonate, NaCl, dl-methionine, vitamins and trace elements. Mice were supplied with drinking water from tap and the water bottles were changed once a week.

Pectin Sources

The pectin with a DE of 7 was obtained from CP Kelko.

Induction of Mucositis and Readouts

Doxorubicin was dissolved in sterile 0.9% sodium chloride and stored in aliquots at 4 C. Pectin (7DM) was dissolved in sterile water and administered by gavage to mice for 10 or 11 days, twice a day at 3 mg/day. On day 8, doxorubicin was injected intra-peritoneal at 10 mg/kg concentration. Mice were sacrificed on day 10 (48 hour doxorubicin) or day 11 (72 hour doxorubicin). Animals receiving water by gavage served as controls. After the collection of tissue samples, mice were sacrificed by cervical dislocation.

TLR2 Blocking in Mice

TLR2 blocking antibody, clone T2.5 (InvivoGen, Toulouse, France) was administered IP at 10 mg/kg one hour prior to doxorubicin treatment.

Neutrophil Count

Peritoneal lavage was collected with 2 ml PBS to collect peritoneal neutrophil influx. The total number of living cells in the peritoneal lavage was counted using a Z™ Series coulter Counter® (Beckman Coulter, Brea, Calif., USA). The lavage was diluted at 500,000 cells/ml and 100 μl of cell solution was applied for cytospin preparation. The cytospin slides were stained with Giemsa stain (Merck Millipore, Billerica, Mass., USA) for 1 hour at room temperature. The stained slides were scanned in a Hamamatsu slide scanner (Hamamatsu photonics, Japan) and neutrophils were counted using morphological features in 250 cells. The total number of neutrophils were calculated using the total cell count in peritoneum and the neutrophoil counts from cytospin preparations.

| Effect of 48 hour doxorubicin treatment on neutrophil count | | |
|---|---|---|
| Mice groups | Total number of neutrophils | Relative increase in neutrophils |
| Control (n = 6) | 3.97E+06 ± 2.39E+06 | 1.0 |
| Pectin DE7 (n = 6) | 2.97E+06 ± 1.29E+06 | 0.7 |
| Doxorubicin (n = 6) | 2.23E+08 ± 6.74E+07 | 56.2 |
| Pectin DE7 + Doxorubicin (n = 5) | 5.44E+07 ± 2.30E+07 | 13.7 |
| TLR2 blocking + Doxorubicin (n = 6) | 7.04E+07 ± 7.30E+07 | 17.7 |
| TLR2 blocking (n = 5) | 8.96E+06 ± 7.90E+06 | 2.3 |

As can be seen from the data, doxorubicin induced mucositis increases the neutrophil count by 56 times. Blocking TLR2 either by the TLR2 blocking antibody clone T2.5 or pectin DE7 significantly reduced the neutrophil count, demonstrating that pectin acts as an anti-inflammatory agent.

Example 7

Pectin Has a Positive Effect on Health Beneficial Microbes

Digesta Collection

The pig fecal samples were collected on day 14 and 28 during the experimental diet feeding (example 4). After the fecal collection period, animals were anesthetized and euthanized. Digesta samples were collected from terminal ileum, proximal colon, mid colon and distal colon. Part of each digesta was stored in 1.5 mL Eppendorf tubes for analysis of microbiota composition and SCFA. These tubes were immediately frozen in liquid nitrogen and stored at −80° C. The remaining amount of digesta was immediately stored at −20° C. until further analysis.

DNA Extraction and Microbiota Analysis

Microbial DNA was extracted from 250 mg of digesta by using a fecal DNA extraction protocol (Salonen A, Nikkilä J, Jalanka-Tuovinen J, Immonen O, Rajilié-Stojanovié M, Kekkonen R A, Palva A & de Vos W M. 2010. Comparative analysis of fecal DNA extraction methods with phylogenetic microarray: Effective recovery of bacterial and archaeal DNA using mechanical cell lysis. Journal of Microbiological Methods, 81: 127-134). The DNA is isolated by sequential precipitations and finally purified by using the QIAamp DNA Stool Mini Kit columns (Qiagen, Hilden, Germany) according to the manufacturer's recommendations. 16S rRNA gene was amplified and sequenced in paired-end mode by using the MiSeq platform (Illumina).

Sequence Analysis

Raw Illumina fastq files were demultiplexed, quality-filtered and analyed using QIIME 1.9.0.

| Relative abundance of *Prevotella* species in the microbiota compostion of experimental fed pigs | | | | |
|---|---|---|---|---|
| Diet | Pectin | Fecal sample | Relative abundance* | Relative increase** |
| A | control | Terminal ileum | 0 | — |
| A | control | Proximal colon | 0.05 | 1 |
| A | control | Mid colon | 0.11 | 1 |
| A | control | Distal colon | 0.09 | 1 |
| B | DE 33 | Terminal ileum | 0 | — |
| B | DE 33 | Proximal colon | 0.51 | 9.99 |
| B | DE 33 | Mid colon | 0.58 | 5.49 |
| B | DE 33 | Distal colon | 0.55 | 6.16 |
| C | DE 55 | Terminal ileum | 0 | — |
| C | DE 55 | Proximal colon | 0.49 | 9.55 |
| C | DE 55 | Mid colon | 0.41 | 3.90 |
| C | DE 55 | Distal colon | 0.45 | 5.07 |
| D | Soy Bean | Terminal ileum | 0 | — |
| D | Soy Bean | Proximal colon | 0.21 | 4.04 |
| D | Soy Bean | Mid colon | 0.22 | 2.09 |
| D | Soy Bean | Distal colon | 0.30 | 3.36 |

*The relative abundance is the % of 16S rRNA data of *Prevotella* in the total data set obtained through Illumina sequencing
**The relative increase is the fold increase in % of *Prevotella* 16S rRNA in the total data set. i.e. the relative abundance determined for a specific pectin fed sample divided by the control sample.

Surprisingly, addition of pectin to the diet leads to an increased prevalence of Prevotella species in the gut (which is an indicator of health, see Wu G D, Chen J, Hoffmann C, Bittinger K, Chen Y Y, Keilbaugh S A, Bewtra M, Knights D, Walters W A, Knight R, Sinha R, Gilroy E, Gupta K, Baldassano R, Nessel L, Li H, Bushman F D & Lewis J D. 2011. Linking long-term dietary patterns with gut microbial enterotypes. Science 334:105-108).

All these examples clearly and surprisingly show that the specific pectins show improvements, which are significant.

The invention claimed is:

1. A method to ameliorate or to lessen immune-mediated diseases or inflammatory diseases caused by activation of TLR2, wherein the method comprises administering by ingestion to a patient in need thereof a mixture of esterified pectins comprising an effective amount between 0.01 and 5 g per kg body weight of the patient of a low esterified pectin having a degree of esterification (DE) of less than 55% obtained from de-esterification of methylated pectin, wherein the patient is an animal selected from the group consisting of human, avian, bovine, canine, equine, galline, feline, hircine, lapine, musteline, ovine, piscine, porcine and vulpine animals.

2. The method according to claim 1, wherein the DE of the low esterified pectin is less than 50%.

3. The method according to claim 1, wherein the DE of the low esterified pectin is at least 1%.

4. The method according to claim 1, wherein the DE of the low esterified pectin is at least 2%.

5. The method according to claim 1, wherein the DE of the low esterified pectin is at least 3%.

6. The method according to claim 1, wherein the administering is practiced by feeding a food or feed formulation which comprises the mixture of esterified pectins to the patient.

7. The method according to claim 1, wherein the DE of the low esterified pectin is less than 33%.

8. The method according to claim 1, wherein the DE of the low esterified pectin is less than 22%.

9. The method according to claim 7, wherein the DE of the low esterified pectin is at least 1%.

10. The method according to claim 8, wherein the DE of the low esterified pectin is at least 1%.

* * * * *

SEQUENCE LISTING

<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: forward primer

<400> SEQUENCE: 1
gcgcaccggt atgccacata ctttgtggat gg               32

<210> SEQ ID NO 2
<211> LENGTH: 31
<212> TYPE: DNA
<213> ORGANISM: Artificial Sequence
<220> FEATURE:
<223> OTHER INFORMATION: reverse primer

<400> SEQUENCE: 2
gcgcggatcc gtgacattcc gacaccgaga g               31